(12) United States Patent
Soomro

(10) Patent No.: US 8,873,419 B2
(45) Date of Patent: Oct. 28, 2014

(54) LINK ASSESSMENT BEFORE TERMINATING ALTERNATE CONNECTION DURING HETEROGENEOUS NETWORK HANDOVERS

(75) Inventor: Amjad A. Soomro, Hopewell Junction, NY (US)

(73) Assignee: Koninklijke Philips N.V., Eindhoven (NL)

( * ) Notice: Subject to any disclaimer, the term of this patent is extended or adjusted under 35 U.S.C. 154(b) by 164 days.

(21) Appl. No.: 13/634,257

(22) PCT Filed: Feb. 24, 2011

(86) PCT No.: PCT/IB2011/050778
§ 371 (c)(1),
(2), (4) Date: Sep. 12, 2012

(87) PCT Pub. No.: WO2011/117764
PCT Pub. Date: Sep. 29, 2011

(65) Prior Publication Data
US 2013/0003595 A1    Jan. 3, 2013

Related U.S. Application Data

(60) Provisional application No. 61/317,993, filed on Mar. 26, 2010.

(51) Int. Cl.
*H04W 24/00* (2009.01)
*H04W 48/18* (2009.01)
*H04W 72/04* (2009.01)
*H04W 88/06* (2009.01)

(52) U.S. Cl.
CPC .............. *H04W 48/18* (2013.01); *H04W 24/00* (2013.01); *H04W 72/04* (2013.01); *H04W 88/06* (2013.01)
USPC .......................................... 370/252; 370/329

(58) Field of Classification Search
None
See application file for complete search history.

(56) References Cited

U.S. PATENT DOCUMENTS 5,301,356 A * 4/1994 Bodin et al. .................. 455/436
6,804,532 B1 * 10/2004 Moon et al. ................. 455/552.1
(Continued)

FOREIGN PATENT DOCUMENTS

| EP | 1665855 B1 | 11/2007 |
| WO | 2004109992 A1 | 12/2004 |
| WO | 2006050206 A1 | 5/2006 |

OTHER PUBLICATIONS

Boysen, E. S., et al.; Proactive Handover in Heterogeneous Networks using SIPs; 2008; IEEE Trans. on 7th Intl. Conf. on Networking; pp. 719-724.
Boysen, E. S., et al.; Proactive Handover using SIP; 2008; North Atlantic Treaty Organisation—Research & Technology Organisation; RTO-MP-IST-083; pp. 17-1-17-10.
Shin, S., et al.; Reducing MAC Layer Handoff Latency in IEEE 802.11 Wireless LANs; 2004; MobiWac'04; Philadelphia, PA.; 8 pages.

*Primary Examiner* — Anh-Vu Ly
*Assistant Examiner* — Hashim Bhatti

(57) ABSTRACT

When providing wireless communication capability for patient monitoring devices (PMDs) (12) in a hospital environment, the quality of a newly established wireless link is evaluated to ascertain that it is meeting quality thresholds before dropping a previous wireless link. A plurality of new links iteratively can be established and their quality assessed, if previous new network link quality does not meet required quality thresholds, until a new link is established that has a quality equal to or greater than the predetermined threshold level. Optionally, two or more links may be maintained that have signal qualities above the predetermined threshold in order to provide link redundancy for highly sensitive patient monitoring applications, such as a link between a critical patient's PMD and a nurses station, to ensure communication there between. In this manner, autonomous generation of link quality assessment reports for use by the other communicating entity or entities is facilitated.

20 Claims, 4 Drawing Sheets

(56) References Cited

U.S. PATENT DOCUMENTS

| | | | |
|---|---|---|---|
| 7,411,491 B2* | 8/2008 | Klabunde et al. | 340/539.12 |
| 2005/0053003 A1* | 3/2005 | Cain et al. | 370/235 |
| 2005/0059400 A1* | 3/2005 | Jagadeesan et al. | 455/436 |
| 2005/0068965 A1 | 3/2005 | Lin et al. | |
| 2006/0277298 A1 | 12/2006 | Kim et al. | |
| 2008/0280614 A1 | 11/2008 | Zuniga et al. | |
| 2009/0036132 A1 | 2/2009 | Liu et al. | |
| 2009/0080344 A1* | 3/2009 | Park et al. | 370/254 |
| 2009/0219894 A1 | 9/2009 | Jee et al. | |
| 2010/0248742 A1* | 9/2010 | Song et al. | 455/456.1 |

\* cited by examiner

LINK ASSESSMENT BEFORE TERMINATING ALTERNATE CONNECTION DURING HETEROGENEOUS NETWORK HANDOVERS

CROSS REFERENCE TO RELATED APPLICATIONS

This application claims the benefit of U.S. provisional application Ser. No. 61/317,993 filed Mar. 26, 2010, which is incorporated herein by reference.

The present innovation finds application in medical patient monitoring systems, particularly with regard to physiologic monitoring systems. However, it will be appreciated that the described techniques may also find application in other monitoring systems, other healthcare information collection scenarios, other status monitoring techniques, and the like.

A typical wireless patient monitoring system (PMS) includes: 1) one or more patient monitoring devices (PMD); 2) a patient information processing server (PIPS); and, 3) a patient database server (PDS). The PMD, the PIPS and the PDS are connected in a network topology. Typically, a hospital's IP network is a wired Ethernet network. The PIPS and the PDS are connected to the wired hospital IP network. The wireless access network which connects the mobile PMD to the hospitals IP network may be based on proprietary or standardized local area network (LAN) technologies such as IEEE 802.11.

The PMD gathers a patient's physiological data (ECG, SpO2, etc.) and sends it to the PIPS where the data is analyzed and displayed. The data from a patient may also be stored on a PDS. The data transmission from a patient monitor to a patient information display server traverses a wireless access network and the wired hospitals IP network. Life-critical patient monitoring systems are error-sensitive, i.e. they can only tolerate a small number of transmission errors, and they are delay-sensitive, i.e. they require data to be transmitted from the PMD to the PIPS within a certain limited delay bound. Also, a key performance requirement for PMDs is low power consumption, which allows PMDs to operate for long periods of time without the need to be recharged or have their batteries changed.

The device based mechanism described by Shin et al. in "Reducing MAC Layer Handoff Latency in IEEE 802.11 Wireless LANs" (MobiWac '04, October 2004), while simple to implement, does not prevent time and energy intensive scanning for candidate networks due to outdated cache entries. While this device may provide limited information about candidate networks such as access point channel and MAC address, it falls short of providing additional information such as network utilization, which would be critical for intelligent access network decisions.

While IEEE 802.21 provides an interesting framework for distribution of access network information its drawbacks for use in PMS include a lack of specification of the manner in which the information is gathered, and therefore the quality of the information is implementation dependent and may be insufficient. Another drawback is that its signaling overhead may require too much bandwidth for proprietary radio technologies. Additionally, IEEE 802.21 compliance increases power consumption, for example scan requests etc., which is detrimental to mobile patient monitoring devices.

Some systems make measurements of link quality and send it to a centralized server that makes the decision of when to initiate a handover. Once the current link quality has been assessed as not meeting required quality thresholds, a new link is established and the previous link dropped. However, the new established link may not meet quality thresholds due to several reasons, for example, a mobile user may have moved out of the coverage area of the new wireless link since the last assessment was done on that link before establishing the new connection. If that is the case, then the user is left with a link with degraded quality. For highly quality-of-service-sensitive applications, such as patient monitoring, it is desirable to have connections with good link quality at all times, and this situation would not be acceptable.

The present application provides new and improved systems and methods for providing a minimum level of communication link quality in a healthcare environment, which overcome the above-referenced problems and others.

In accordance with one aspect, a method of providing a mobile patient monitoring device (MPMD) with an optimized quality over a wireless network in medical environment comprises establishing a first communication link between a MPMD and a first wireless network via which the MPMD communicates with a healthcare Internet protocol (IP) network or some other IP network outside a healthcare environment, and evaluating a quality of the first communication link. The method further comprises, in response to determining that the quality of the first communication link is below a predetermined threshold level, establishing a second communication link with a second wireless network via which the MPMD communicates with the healthcare Internet protocol (IP) network, and evaluating a quality of the second communication link after it is established. Additionally, in response to determining whether the quality of the second communication link is below the predetermined threshold level, the first communication link is maintained if the quality of the second communication link is below the predetermined threshold level. In response to the quality of the second communication link being not below the predetermined threshold level, the first communication link is terminated.

In accordance with another aspect, a system that facilitates providing a mobile patient monitoring device (MPMD) with a optimum quality over a wireless network in medical environment comprise an MPMD coupled to a first wireless network via which the MPMD communicates with a healthcare Internet protocol (IP) network, and a patient information processing server (PIPS) coupled to the healthcare IP network. The system further comprises wireless link management middleware that includes a processor configured to evaluate a quality of the first communication link, and in response to a determination that the quality of the first communication link is below a predetermined threshold level, to establish a second communication link with a second wireless network via which the MPMD communicates with the healthcare Internet protocol (IP) network. The processor is further configured to evaluate a quality of the second communication link after it is established, and in response to a determination that the quality of the second communication link is below the predetermined threshold level, to maintain the first communication link if the quality of the second communication link is below the predetermined threshold level. In response to the quality of the second communication link being not below the predetermined threshold level, the processor terminates the first communication link.

In accordance with another aspect, an (MPMD) with a optimum quality over a wireless network in medical environment comprises wireless link management middleware that includes a processor programmed to execute stored instructions to evaluate a quality of a first communication link with a first wireless network via which the MPMD communicates with a healthcare Internet protocol (IP) network, and in response to a determination that the quality of the first communication link is below a predetermined threshold level, to establish a second communication link with a second wireless network via which the MPMD communicates with the healthcare Internet protocol (IP) network. The processor is further programmed to evaluate a quality of the second communication link after it is established, and in response to a determination that the quality of the second communication link is below the predetermined threshold level, to maintain the first communication link if the quality of the second communication link is below the predetermined threshold level. In response to the quality of the second communication link being not below the predetermined threshold level, the processor terminates the first communication link.

One advantage is that consistent quality is maintained for the patient monitoring device.

Another advantage resides in power savings for the patient monitoring device.

Still further advantages of the subject innovation will be appreciated by those of ordinary skill in the art upon reading and understanding the following detailed description.

The drawings are only for purposes of illustrating various aspects and are not to be construed as limiting.

To overcome the aforementioned problems, the described systems and methods assess the quality of a newly established wireless link to ascertain that it meets quality thresholds before dropping a previous wireless link. Additionally, a plurality of new links can be established and their quality assessed, if previous new network link quality does not meet required quality thresholds. In this manner, autonomous generation of link quality assessment reports for use by the other communicating entity or entities is facilitated.

Figure 1:
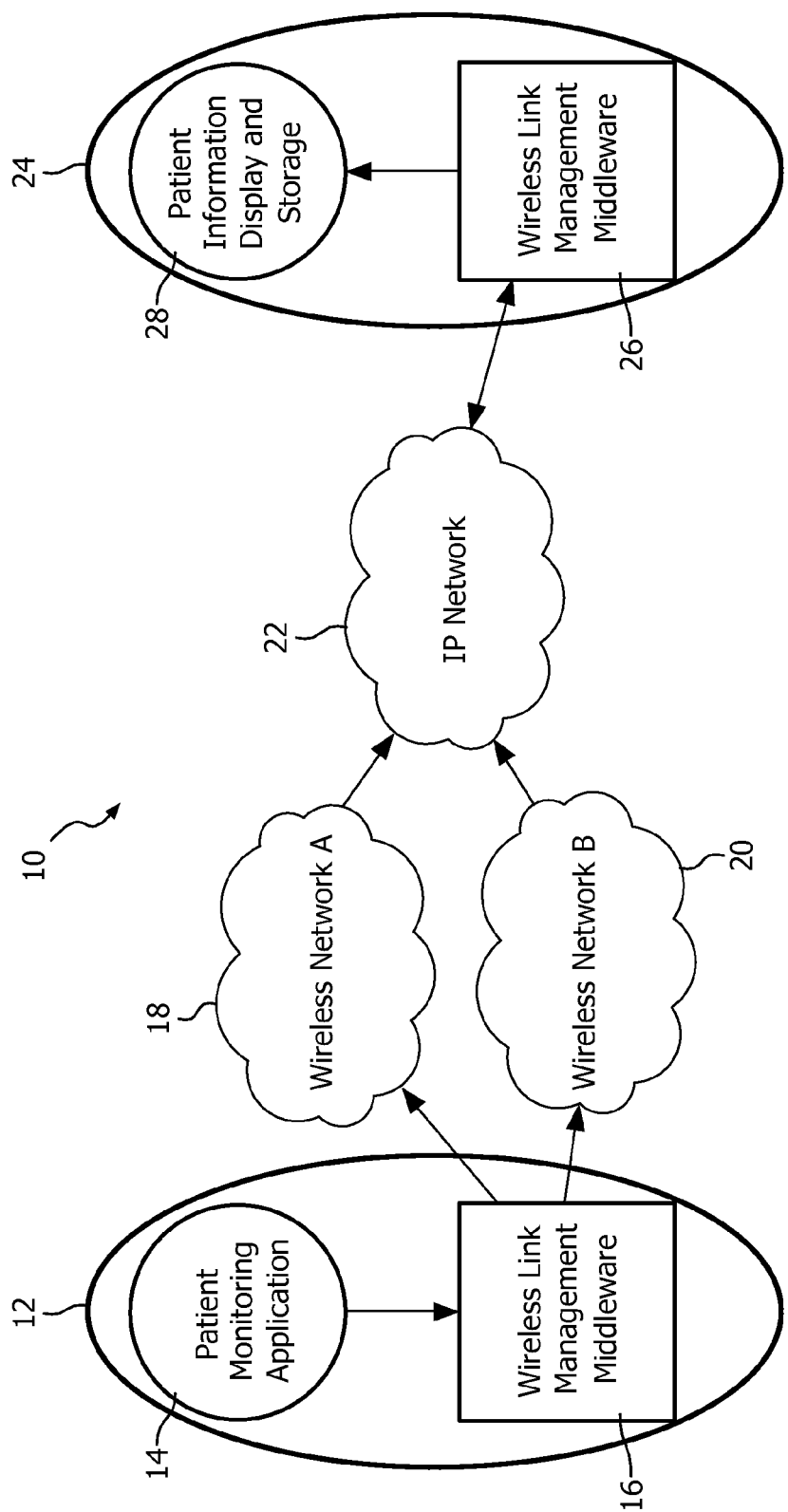
FIG. 1 illustrates a system that facilitates providing a minimum quality level for a mobile patient monitoring device (MPMD) in a healthcare environment.

FIG. 1 illustrates a system 10 that facilitates providing a minimum quality level for a mobile patient monitoring device (MPMD) 12 in a hospital or healthcare environment. The MPMD includes a patient monitoring application 14 that monitors one or more physiological parameters of the patient (e.g., heart rate, respiratory rate, SpO2, temperature, blood pressure, etc.). The MPMD also includes wireless link management middleware 16 (e.g., hardware and software) for communicating over one or more wireless networks in the hospital environment. For instance, the middleware 16 facilitates transmitting information to and receiving information from a first wireless network 18, a second wireless network 20, up to an Nth wireless network (not shown). The wireless networks are coupled to and communicate with a healthcare Internet protocol (IP) network 22, which in turn is operatively coupled to a patient information processing server (PIPS) 24.

The PIPS includes wireless link management middleware 26 (e.g., hardware and software for communicating with the IP network and/or over one or more wireless networks in the healthcare environment. "Healthcare environment" as used herein may mean a hospital or other patient care facility. In another example a healthcare environment may be an ambulance or other patient transport wherein the MPMD communicates locally with a PIPS and/or via a cellular connection with the PIPS and/or one or more wireless networks. In another example, a healthcare environment exists wherever the PMDM is located, such as when a PMDM is located in a patient's home and monitors the patient to provide physiological patient data over an IP network to a local or remote PIPS. The PIPS also includes a patient information display and storage (PIDS) 28 component (e.g., processor, memory, and display, etc.) at which patient information received from the MPMD is stored and displayed.

In one embodiment, the middleware component 16 detects when a quality of a communication link between a first network 18 and the MPMD 12 falls below a predetermined threshold, and initiates a new communication link between the MPMD and a second network 20. Before terminating the communication link with the first network, the middleware 16 performs a link quality assessment on the new communication link to ensure that the new communication link has a quality above the predetermined threshold. If not, then the first communication link is maintained to ensure that the MPMD can still communicate with the IP network, while the middleware 16 attempts to establish a another new communication link with the second network 20 or with a third network (not shown), and so on until a new communication link is established that has a quality above the predetermined threshold level. In order to determine whether a end-to-end link or connection (e.g., from the MPMD to the PIPS or another end node such as the IP network) is acceptable, the predetermined threshold comparisons described herein can be made against more than one parameter, each parameter having a predetermined threshold value to compare against. A decision whether a connection is acceptable or not can be based on discrete logic (e.g., included in and/or executed by in the middleware 16, 26) which takes in results of the threshold comparison against one or more parameters with their respective thresholds.

"Quality" of the communication link, or "link quality," as used herein includes various aspects of the communication link that contribute to overall link quality. In one sense, the quality may be the SNR of a received RF waveform. In other respects, the quality of the connection is, in part, determined by the signal quality and other factors that affect the quality of the connection. For example, load on the network, congestion in the network, capacity or bandwidth of the link, etc., may contribute to overall link quality. In addition, the state and quality of the connection may be affected not only by the above factors on the first or immediate link, but also the second link, third link, and so on, of a path to the destination node (i.e., the other end point of the connection), which is why the measurements performed by the described systems and methods are made after a connection is made (i.e. rather than merely estimated beforehand). Pre-connection assessment or estimation of the signal quality does not give complete picture of the quality of service (QoS) that a device can expect.

Optionally, the middleware 16 compares the quality of the communication link between the MPMD and the first network to the quality of the link with the second network, and maintains the link with the better quality while terminating the poorer-quality link in order to conserve battery power at the MPMD. In another embodiment, quality assessments between the MPMD and the network(s) 18, 20 are performed by the middleware 26 in the PIPS 24 (i.e., at the receiver side), in order to conserve battery power in the MPMD.

It will be appreciated that the middleware 16, 26 may include hardware and/or software for performing the described functions, methods, actions, and the like. For instance, the middleware may include a memory or computer-readable medium (not shown) that stores, and one or more processors (not shown) that execute, computer-executable instructions for performing the various functions, actions, steps, methods, etc., described herein. The memory may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

Figure 2:
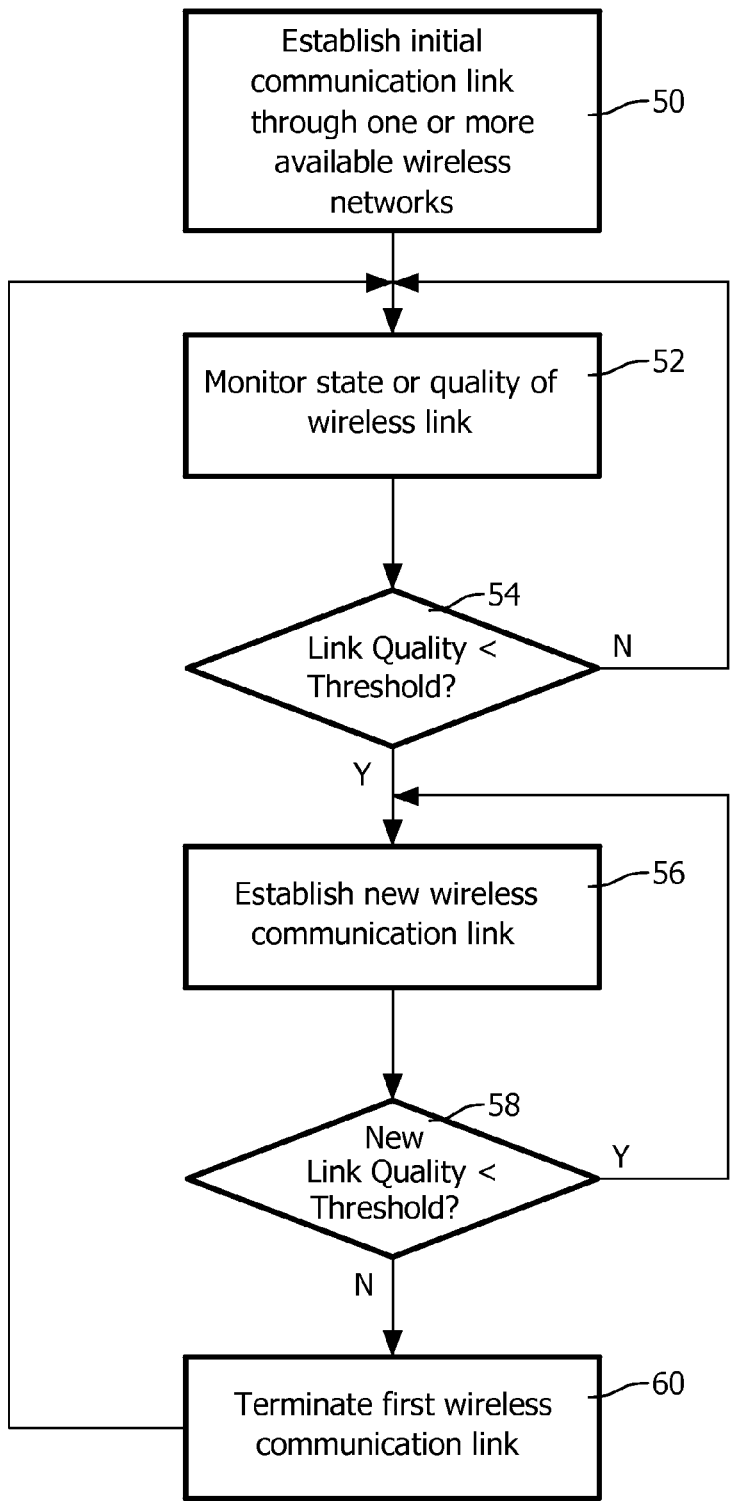
FIG. 2 illustrates a flow diagram of a method in which the condition of a new wireless link is assessed after making a connection to a new network but before dropping the previous or existing wireless link.
Figure 3:
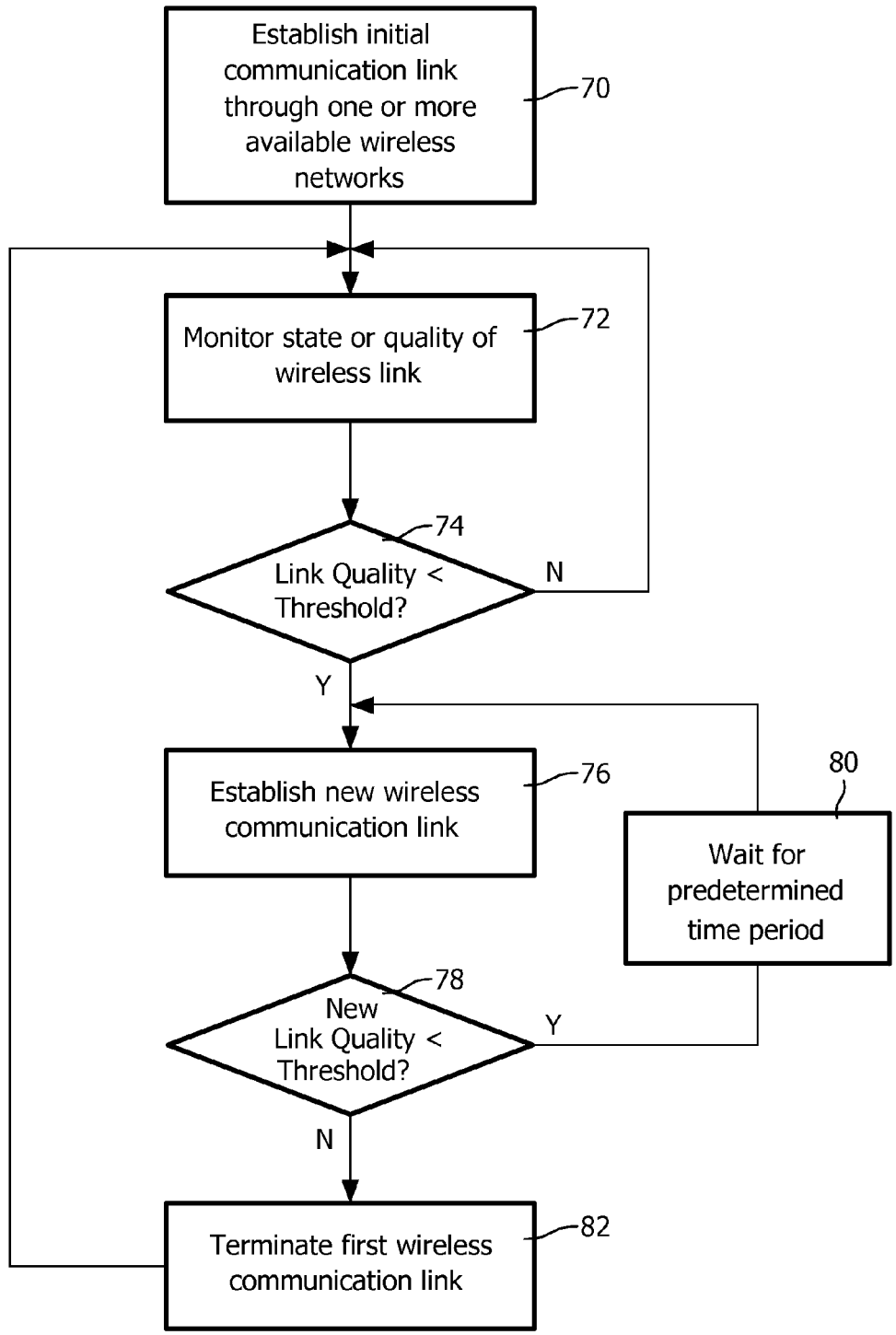
FIG. 3 illustrates a flow diagram of a method in which the condition of a new wireless link is assessed for a predetermined time period after making a connection to a new network but before dropping the previous or existing wireless link, wherein the existing or previous link is terminated if the new link has a quality above a predetermined threshold level within the predetermined time period.
Figure 4:
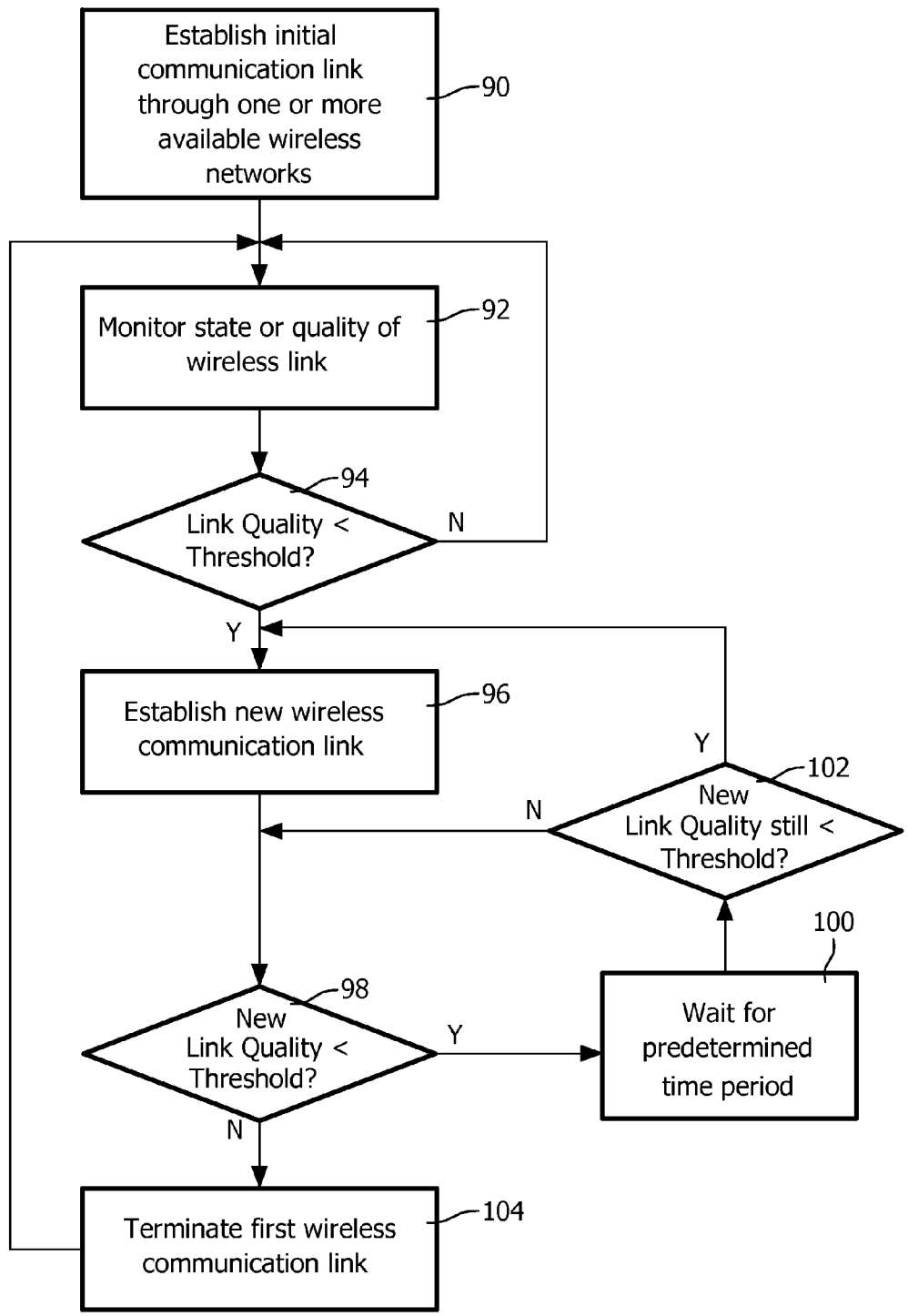
FIG. 4 illustrates a flow diagram of a method in which the condition of a new wireless link is assessed for a predetermined time period after making a connection to a new network but before dropping the previous or existing wireless link, wherein the existing or previous link is terminated if the new link has a quality above a predetermined threshold level within the predetermined time period.

The following embodiments are provided by way of example to describe various manners in which the system of FIG. 1 and the methods of FIGS. 2-4 are employed, and are not to be construed in a limiting manner. In one embodiment, the PIPS 24 (or a receiver) performs the link quality assessment. The MPMD 12 (or sender) gets link assessment information by receiving a link assessment or quality report from the PIPS autonomously, i.e., without explicitly requesting the link quality report. In another embodiment, the MPMD actively requests the link quality report from the PIPS. The link assessment report is a message in a protocol frame at the application layer, session layer, transport layer, network layer, media access layer or the physical layer of the communication link. The link quality report includes a measurement of the link quality at the application layer, session layer, transport layer, network layer, media access layer or the physical layer. Additionally, as an example, the report may include information gleaned by monitoring a number of unsuccessful attempts to transmit packets, a lack of acknowledgements received at the application layer, session layer, transport layer, network layer, media access layer or the physical layer, etc. In another example, a report includes results of measurement of the physical layer bit or packet error rate, media access layer packet error rate, network layer packet error rate, etc. to assess the link quality. In another example, the report includes results of measurement of the physical layer delays, media access layer delays, network layer packet delays, transport layer delays, session layer delays, or application layer delays to assess the link quality. In another example, the report includes results of measurement of the physical layer jitter, media access layer jitter, network layer packet jitter, transport layer jitter, session layer jitter, or application layer jitter to assess the link quality.

In another embodiment, the role of the MPMD 12 or the sender is reversed with the PIPS 24 or receiver. That is, the reports are sent by the MPMD or sender autonomously (or upon request by the PIPS), and they are received by the PIPS.

According to another embodiment, the PIPS 24 or receiver establishes a connection with the MPMD 12 or sender (or vice versa) using SIP protocols. In another embodiment, the PIPS 24 or receiver establishes a connection with the MPMD 12 or sender (or vice versa) using H.323 protocol. The connections may be unidirectional (send or receive only) or send-and-receive.

Link Quality assessment may be performed by the MPMD 12 or by the PIPS 24. If performed by the PIPS, a link quality report is sent to the MPMD as a message in a protocol frame in one or more of the application layer, session layer, transport layer, network layer, media access layer, or the physical layer. A request is sent from the MPMD to the PIPS to have the PIPS assess the link quality, and may include a request to measure of the link quality at the application layer, session layer, transport layer, network layer, media access layer, or the physical layer.

In another embodiment, the MPMD 12 or sender does a link quality assessment by measuring the link quality at the application layer, session layer, transport layer, network layer, media access layer or the physical layer as seen at the sender. For example, The MPMD may monitor the number of unsuccessful attempts to transmit packets, the lack of acknowledgements received at the application layer, session layer, transport layer, network layer, media access layer, or the physical layer, etc.

In the case of duplex or half duplex connections, the MPMD 12 or sender measures the physical layer bit or packet error rate, media access layer packet error rate, network layer packet error rate, etc., to assess the link quality. The MPMD or sender can also measure the physical layer delays, media access layer delays, network layer packet delays, transport layer delays, session layer delays, or application layer delays to assess the link quality. Additionally or alternatively, the MPMD or sender measures the physical layer jitter, media access layer jitter, network layer packet jitter, transport layer jitter, session layer jitter, or application layer jitter to assess the link quality.

In another embodiment, the response from the PIPS 24 or receiver includes one or more of foregoing parameters (e.g., link quality as a function of unsuccessful packet transmission attempts and/or lack of acknowledgements received at various link layers, one or more of packet error rate, jitter, and delays at one or more of the link layers, etc.).

In another embodiment, the role of the MPMD 12 or sender is reversed with the PIPS 24 or receiver. That is, the requests are sent by the PIPS or a receiver and the responses are generated by the MPMD or sender.

In another embodiment, the assessments of the link quality as a function of one or more of packet error rate, jitter, and delays at one or more of the link layers, etc., are done at the PIPS 24 or receiver.

In one embodiment, the MPMD or sender transmits real-time data using an RTP (IETF RFC 3550) protocol.

In another embodiment, the wireless networks 18, 20 include communication technologies associated with one or more of: IP Multimedia Subsystem (IMS), general packet radio service (GPRS), universal mobile telecommunication system (UMTS), code-division multiple access (CDMA), CDMA2000, Interim Standard 95 (IS-95), global system for mobile communication (GSM), CDMA 1x, CDMA 1X evolution data optimized EV-DO, world-wide interoperability for microwave access (WiMAX), IEEE 802.11, IEEE 802.15, IEEE 802.16, IEEE 802.21, wireless fidelity (Wi-Fi), UMTS over wideband CDMA (W-CDMA), UMTS over time-division duplex (TDD), CDMA 3X EVDO, high-speed packet access (HSPA) D, HSPA U, enhanced data rates for GSM evolution (EDGE), Bluetooth, Zigbee, ultra wideband (UWB), long term evolution (LTE), Wi-Bree etc. The wireless networks 18, 20 may furthermore employ a common wireless technology or different wireless technologies.

FIG. 2 illustrates a flow diagram of a method in which the condition of a new wireless link is assessed after making a connection to a new network but before dropping the previous or existing wireless link. At 50, an initial communication link (e.g., a first link) is established between a MPMD and a PIPS over an available wireless network. The status (e.g., quality of service) of the initial communication link is monitored (e.g., continuously, periodically, etc.), at 52. At 54, a determination is made regarding whether the quality in the existing link is below a minimum acceptable threshold level (e.g., 50%, 60%, 75%, etc., of a maximum level). If the quality for the existing link is not below the threshold level, then the method reverts to 52 for continued monitoring of the quality of the existing link. If the quality is determined to be below the minimum threshold level, then at 56, a new (e.g., second) wireless communication link is established. The new link may be established on the same wireless network or on a different network. For instance, if the initial or existing link quality is diminished due to an increased distance between the MPMD and an access point providing the existing link (e.g., as a result of the patient moving away from the access point), then the new link is established on a new network providing a better quality. In another example, the quality of the existing link may be degraded due to limited bandwidth at a serving access point, in which case the new link may be established on the original or first network using a different access point. Alternatively, the new link may be established on a different network.

At 58, a determination is made regarding whether the quality of the new link is below the predetermined acceptable threshold. If so, then the method reverts to 56, where yet another link is established (e.g., a third link, in this example). The original "new" link (e.g., the second link in this example) may be terminated at this point or may be retained. If the new (second) link has a quality above the predetermined threshold, then at 60, the initial (first) link is terminated. In this manner, a new link having a predetermined minimum quality is established and evaluated before the original link is terminated to ensure a minimum quality of service for the MPMD.

FIG. 3 illustrates a flow diagram of a method in which the condition of a new wireless link is assessed for a predetermined time period after making a connection to a new network but before dropping the previous or existing wireless link, wherein the existing or previous link is terminated if the new link has a quality above a predetermined threshold level within the predetermined time period. At 70, an initial communication link (e.g., a first link) is established between a MPMD and a PIPS over an available wireless network. The status (e.g., quality of service) of the initial communication link is monitored (e.g., continuously, periodically, etc.), at 72. At 74, a determination is made regarding whether the quality in the existing link is below a minimum acceptable threshold level (e.g., 40%, 45%, 60%, etc., of a maximum level). If the quality for the existing link is not below the threshold level, then the method reverts to 72 for continued monitoring of the quality of the existing link. If the quality is determined to be below the minimum threshold level, then at 76, a new (e.g., second) wireless communication link is established. The new link may be established on the same wireless network or on a different network. At 78, a determination is made regarding whether the quality of the new link is below the predetermined acceptable threshold. If so, then at 80 a predetermined time period is permitted to elapse before the method reverts to 76 for generation of another new wireless communication link. If the new (second) link has a quality above the predetermined threshold, then at 82, the initial (first) link is terminated. In this manner, a new link having a predetermined minimum quality is established and evaluated before the original link is terminated to ensure a minimum quality of service for the MPMD. That is, the method may be iterated a pre-determined number of times or for a pre-determined time period before dropping the previous wireless link.

FIG. 4 illustrates a flow diagram of a method in which the condition of a new wireless link is assessed for a predetermined time period after making a connection to a new network but before dropping the previous or existing wireless link, wherein the existing or previous link is terminated if the new link has a quality above a predetermined threshold level within the predetermined time period. At 90, an initial communication link (e.g., a first link) is established between a MPMD and a PIPS over an available wireless network. The status (e.g., quality of service) of the initial communication link is monitored (e.g., continuously, periodically, etc.), at 92. At 94, a determination is made regarding whether the quality in the existing link is below a minimum acceptable threshold level (e.g., 40%, 45%, 60%, etc., of a maximum level). If the quality for the existing link is not below the threshold level, then the method reverts to 92 for continued monitoring of the quality of the existing link. If the quality is determined to be below the minimum threshold level, then at 96 a new (e.g., second) wireless communication link is established. The new link may be established on the same wireless network or on a different network. At 98, a determination is made regarding whether the quality of the new link is below the predetermined acceptable threshold. If so, then at 100 a predetermined time period is permitted elapse (e.g., 10 seconds, 60 seconds, etc.). After the predetermined time period has expired, then at 102, the quality of the new communication link is again evaluated to determine whether it is above the predetermined minimum threshold. If the new link quality does not rise and/or stay above the predetermined minimum threshold level by the end of the predetermined time period, then the method reverts to 96, where yet another link is established (e.g., a third link, in this example). The original "new" link (e.g., the second link in this example) may be terminated at this point or may be retained. If the new (second) link has a quality above the predetermined threshold, then at 104, the initial (first) link is terminated. In this manner, a new link having a predetermined minimum quality is established and evaluated before the original link is terminated to ensure a minimum quality of service for the MPMD. That is, the method may be iterated for a predetermined time period or a predetermined number of times, and if the new link quality is not above thresholds, an additional new connection is established and assessed through a different wireless link.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A method of providing a mobile patient monitoring device (MPMD) with an optimized link quality over a wireless network in medical environment, comprising:

establishing a first communication link between a MPMD and a first wireless network via which the MPMD communicates with a healthcare Internet protocol (IP) network;

evaluating a quality of the first communication link;

in response to determining that the quality of the first communication link is below a predetermined threshold level, establishing a second communication link with a second wireless network via which the MPMD communicates with the healthcare Internet protocol (IP) network;

evaluating a quality of the second communication link after it is established;

in response to determining whether the quality of the second communication link is below the predetermined threshold level, maintaining the first communication link if the quality of the second communication link is below the predetermined threshold level; and in response to the quality of the second communication link being not below the predetermined threshold level, terminating the first communication link;

wherein the MPMD requests quality information reports from a patient information processing server (PIPS) in order to determine whether to terminate the first communication link.

2. The method according to claim 1, wherein the qualities of the first and second communication links are evaluated by the MPMD.

3. The method according to claim 1, wherein the qualities of the first and second communication links are evaluated by a patient information processing server that is in communication with the healthcare IP network.

4. The method according to claim 1, further including:
evaluating the quality of the first and second communicating links by measuring a link quality at a specific layer of the communication links, the layer being one or more of:
an application layer;
a session layer;
a transport layer;
a network layer;
a media access (MAC) layer; and
a physical layer.

5. The method according to claim 4, further including:
measuring at least one of unsuccessful packet transmission attempts and a lack of acknowledgements received at one or more of the specific layer to evaluate communication link quality.

6. The method according to claim 4, further including:
measuring at least one of packet error rate, delays, and jitter in the specific layer of the communication links to evaluate communication link quality;
wherein the communication links are duplex or half-duplex communication links.

7. The method according to claim 1, further comprising at least one of:
if the quality of second communication link is below the predetermined threshold level, waiting a predetermined time period after evaluating the second communicating link, and reevaluating the quality of second communication link;
terminating the first communication link once the quality of the second communication link is above the predetermined threshold level; and
terminating the second communication link, establishing a third communication link, evaluating the quality thereof, and terminating the first communication link if the quality of the third communication link is above the predetermined threshold level.

8. The method according to claim 1, wherein the first and second wireless networks employ different wireless communication protocols, including the wireless communication protocols being two or more of:
IP Multimedia Subsystem (IMS);
GPRS;
UMTS;
CDMA2000;
IS-95;
GSM;
CDMA;
CDMA 1x;
CDMA 1X EV-DO;
WiMAX;
IEEE 802.11;
IEEE 802.15;
IEEE 802.16;
IEEE 802.21;
Wi-Fi;
UMTS over W-CDMA;
UMTS over TDD;
CDMA 3X EVDO;
HSPA D;
HSPA U;
EDGE;
Bluetooth;
Zigbee;
UWB;
LTE; and
Wi-Bree.

9. A non-transitory computer-readable medium carrying software for controlling a processor to configure and perform the method of claim 1.

10. A system that facilitates providing a mobile patient monitoring device (MPMD) with an optimum link quality over a wireless network in medical environment, comprising:
an MPMD coupled to a first wireless network via which the MPMD communicates with a healthcare Internet protocol (IP) network;
a patient information processing server (PIPS) coupled to the healthcare IP network; and
wireless link management middleware that includes a processor programmed to:
establish a first communication link between the MPMD and a first wireless network via which the MPMD communicates with the healthcare Internet protocol (IP) network;
evaluate a quality of the first communication link;
in response to determining that the quality of the first communication link is below a predetermined threshold level, establish a second communication link with a second wireless network via which the MPMD communicates with the healthcare Internet protocol (IP) network;
evaluate a quality of the second communication link after it is established;
in response to determining whether the quality of the second communication link is below the predetermined threshold level, maintain the first communication link if the quality of the second communication link is below the predetermined threshold level; and
in response to the quality of the second communication link being not below the predetermined threshold level, terminate the first communication link;

wherein the MPMD requests quality information reports from the patient information processing server (PIPS) in order to determine whether to terminate the first communication link.

11. A system that facilitates providing a mobile patient monitoring device (MPMD) with an optimum link quality over a wireless network in medical environment, comprising:
   an MPMD coupled to a first wireless network via which the MPMD communicates with a healthcare Internet protocol (IP) network;
   a patient information processing server (PIPS) coupled to the healthcare IP network; and
   wireless link management middleware that includes a processor configured to:
   evaluate a quality of a first communication link;
   in response to a determination that the quality of the first communication link is below a predetermined threshold level, establish a second communication link with a second wireless network via which the MPMD communicates with the healthcare Internet protocol (IP) network;
   evaluate a quality of the second communication link after it is established;
   in response to a determination that the quality of the second communication link is below the predetermined threshold level, maintain the first communication link if the quality of the second communication link is below the predetermined threshold level; and
   in response to the quality of the second communication link being not below the predetermined threshold level, terminate the first communication link;
   wherein the MPMD requests quality information reports from the PIPS in order to determine whether to terminate the first communication link.

12. The system according to claim 11, wherein the middleware resides in the MPMD.

13. The system according to claim 11, wherein the middleware resides in the PIPS.

14. The system according to claim 11, wherein the processor is further programmed to evaluate the quality of the first and second communicating links by measuring a link quality at a specific layer of the communication links, the layer being one or more of:
   an application layer;
   a session layer;
   a transport layer;
   a network layer;
   a media access (MAC) layer; and
   a physical layer.

15. The system according to claim 14, wherein the processor is further programmed to measure at least one of packet error rate, delays, and jitter in the specific layer of the communication links to evaluate communication link quality, wherein the communication links are duplex or half-duplex communication links.

16. The method according to claim 14, wherein the processor is further programmed to measure at least one of unsuccessful packet transmission attempts and a lack of acknowledgements received at one or more of the specific layer to evaluate communication link quality.

17. The system according to claim 11, wherein the processor is further programmed to at least one of:
   wait a predetermined time period after evaluating the second communicating link if the quality of second communication link is below the predetermined threshold level, and reevaluate the quality of second communication link;
   terminate the first communication link once the quality of the second is above the predetermined threshold level; and
   terminate the second communication link, establishing a third communication link, evaluating the quality thereof, and terminating the first communication link if the quality of the third communication link is above the predetermined threshold level.

18. The system according to claim 11, wherein the first and second wireless networks employ different wireless communication protocols, including the wireless communication protocols being two or more of:
   IP Multimedia Subsystem (IMS);
   GPRS;
   UMTS;
   CDMA2000;
   IS-95;
   GSM;
   CDMA;
   CDMA 1x;
   CDMA 1X EV-DO;
   WiMAX;
   IEEE 802.11;
   IEEE 802.15;
   IEEE 802.16;
   IEEE 802.21;
   Wi-Fi;
   UMTS over W-CDMA;
   UMTS over TDD;
   CDMA 3X EVDO;
   HSPA D;
   HSPA U;
   EDGE;
   Bluetooth;
   Zigbee;
   UWB;
   LTE; and
   Wi-Bree.

19. An MPMD for use in the system according to claim 11.

20. An (MPMD) with an optimum quality over a wireless network in medical environment, comprising:
   wireless link management middleware that includes a processor programmed to execute stored instructions to:
      evaluate a quality of a first communication link with a first wireless network via which the MPMD communicates with a healthcare Internet protocol (IP) network;
      in response to a determination that the quality of the first communication link is below a predetermined threshold level, establish a second communication link with a second wireless network via which the MPMD communicates with the healthcare Internet protocol (IP) network;
      evaluate a quality of the second communication link after it is established;
      in response to a determination that the quality of the second communication link is below the predetermined threshold level, maintain the first communication link if the quality of the second communication link is below the predetermined threshold level; and
      in response to the quality of the second communication link being not below the predetermined threshold level, terminate the first communication link;
      wherein the MPMD requests quality information reports from a patient information processing server (PIPS) in order to determine whether to terminate the first communication link.

* * * * *